United States Patent [19]

Espitalie et al.

[11] 4,352,673

[45] Oct. 5, 1982

[54] METHOD AND DEVICE FOR DETERMINING THE ORGANIC CARBON CONTENT OF A SAMPLE

[75] Inventors: Jean Espitalie, Le Vesinet; Marcel Madec, Suresnes, both of France; Paul Leplat, Louvain; Jacques Paulet, Emines, both of Belgium

[73] Assignees: Institut Francais du Petrole, Rueil-Malmaison, France; Societe Labofina S.A., Brussels, Belgium

[21] Appl. No.: 219,616

[22] Filed: Dec. 24, 1980

[30] Foreign Application Priority Data

Dec. 28, 1979 [FR] France .............................. 79 32019

[51] Int. Cl.$^3$ ............................................ G01N 31/08
[52] U.S. Cl. ............................ 23/230 EP; 23/230 PC; 422/80
[58] Field of Search ....... 23/230 PC, 230 EP, 230 M; 422/78, 80

[56] References Cited

U.S. PATENT DOCUMENTS

| | | | |
|---|---|---|---|
| 3,880,587 | 4/1975 | Szakasits et al. | 23/230 PC |
| 3,953,171 | 4/1976 | Espitalie et al. | 23/230 PC |
| 4,153,415 | 5/1979 | Espitalie et al. | 23/230 PC |
| 4,213,763 | 7/1980 | Madec et al. | 23/230 PC |

FOREIGN PATENT DOCUMENTS 2449143  5/1975  Fed. Rep. of Germany ... 23/230 PC

*Primary Examiner*—William F. Smith
*Attorney, Agent, or Firm*—Millen & White

[57] ABSTRACT

The method of the invention comprises the successive steps of: (a) heating the sample in an inert atmosphere to a first temperature capable of cracking at least a fraction of the organic material contained in the sample; (b) measuring the amount of organic carbon contained in at least a fraction of the effluent resulting from this cracking; (c) heating the sample in an oxidizing atmosphere to a second temperature at most equal to the first temperature; (d) measuring the amount of organic carbon in the effluent produced by the oxidation of the organic material, and (e) deriving from the above measurements the total organic carbon content of the sample. In order to perform the method of the invention, there is also provided means for performing each of the successive steps. In a further refinement, the method also includes steps for determining the mineral carbon content so that the total carbon content of the sample can be determined.

6 Claims, 3 Drawing Figures

METHOD AND DEVICE FOR DETERMINING THE ORGANIC CARBON CONTENT OF A SAMPLE

BACKGROUND OF THE INVENTION

The present invention relates to a method and a device for determining, in particular, the amount of organic carbon contained in a sample, this method also permits, if necessary, the determination of the mineral carbon content.

Various methods are already known for determining the quantity of carbon contained in liquid samples.

One of these methods, of which some embodiments are described in FRENCH Patent Application 2,265,095 and in U.S. Pat. Nos. 3,296,435 and 3,530,292 consists of oxidizing a sample at a high temperature and measuring the amount of carbon dioxide which is obtained, this amount representing the total quantity of carbon contained in the sample. However, this method does not permit distinguishing between the mineral and the organic carbon in the sample.

According to another method of analyzing a liquid sample, which is described in U.S. Pat. No. 3,607,071 and BRITISH Pat. No. 1,494,906, the sample is subjected to a preliminary treatment to extract the mineral carbon therefrom.

A subsequent oxidation of the remaining fraction of the sample and the measurement of the amount of the so-obtained carbon dioxide so obtained permits determination of the amount of organic carbon. However, this method is time-consuming.

According to another method described in FRENCH Patent Application 2,420,141 and in U.S. Pat. No. 3,672,841, the total amount of carbon contained in a sample is determined by heating the latter in an oxidizing atmosphere to at least 1000° C., and measuring the amount of carbon dioxide produced during this heating step. It is assumed that by subjecting a second sample to a similar treatment at a temperature which does not exceed 600° the measurement of the amount of the carbon dioxide so-produced represents the amount of organic carbon in the sample. The difference between these two results gives the amount of mineral carbon.

In practice, if the first measurement is actually representative of the total amount of carbon contained in the sample, the measurement performed on the second sample can only be valid if the sample contains no carbonate, since carbonates are decomposed under 600° C., or if the carbonate amount is small compared to the amount of organic carbon. In other words, the accuracy in the determination of the amount of organic carbon is not known and the same occurs for the amount of mineral carbon which is derived from the difference between the value of the total carbon amount and the value of the amount of organic carbon.

The method for determining the organic carbon content in a geological sample which is described in BELGIAN Pat. No. 852,335 consists of pyrolyzing a sample in an inert atmosphere, measuring the amount of so-obtained benzene and deriving from this measurement, on the basis of a pre-established chart, the amount of organic carbon contained in the sample. The difficulty of this method lies in the necessity of pre-establishing a chart, and moreover, the accuracy of the results obtained by this method is low.

It is already known from FRENCH Patent application 2,376,414 to pyrolyze a sample in an inert atmosphere so as to measure the sulphur compounds after oxidation of the pyrolysis products.

However this method cannot be applied to the determination of the amount of organic carbon contained in a sample of geological sediment.

With respect to these methods, the object of the present invention is to permit a faster and more accurate determination of the respective amounts of organic and mineral carbon, these results being obtained from a single sample.

BRIEF DESCRIPTION OF THE DRAWINGS

The invention will will become readily understood and all its advantages be clearly apparent from the following description illustrated by the accompanying drawings wherein.

DETAILED DISCUSSION OF THE INVENTION

Figure 1:
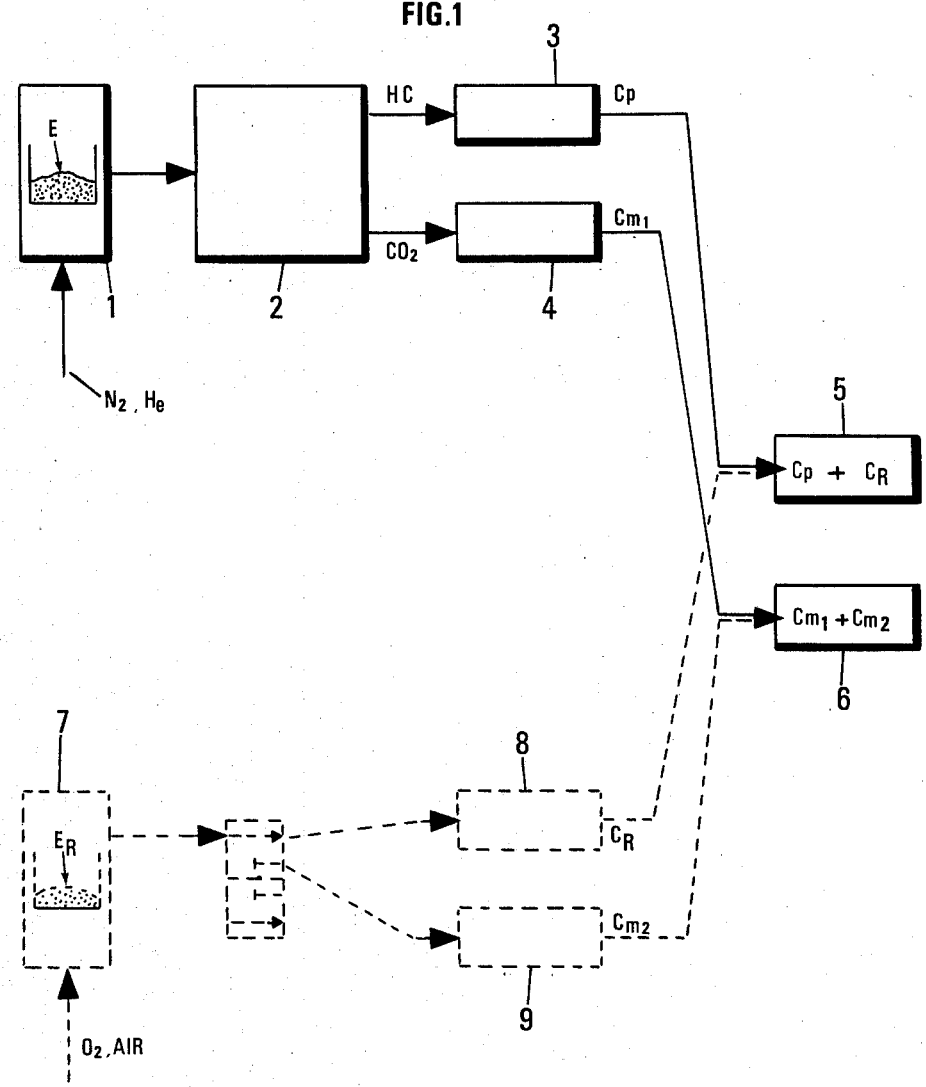
FIG. 1 diagramatically illustrates the method according to the invention.

The process according to the invention, diagrammatically illustrated in FIG. 1, comprises pyrolyzing the sample E in a first heating chamber 1 in an inert atmosphere and at a temperature $\theta_1$ comprised between 500° and 600° C., this pyrolysis producing a cracking of the organic material contained in the sample.

The effluents resulting from this pyrolysis are analyzed in 2 so as to determine, on the one hand, the amount of hydrocarbon products (H-C) and, on the other hand, the amount of carbon dioxide ($CO_2$) produced by the early decomposition of some carbonates when the sample is heated to the temperature $\theta_1$.

These carbonates are, for example but not exclusively, nahcolite (sodium bicarbonate $NaHCO_3$), dawsonite (double carbonate of sodium and aluminium (Na Al $CO_3$, $H_2O$) which are decomposed at temperatures comprised between 200° and 300° C., or also siderite (iron carbonate Fe $CO_3$) whose decomposition temperature lies between 400° and 500° C., etc . . .

From the amount of hydrocarbons or hydrocarbon products is derived at 3, the amount $C_p$ of organic carbon contained in the effluents resulting from the pyrolysis of the sample in the inert atmosphere.

There is similarly evaluated at 4 the amount of mineral carbon $C_{m1}$ corresponding to the carbon dioxide produced by the early decomposition of some carbonates.

The values $C_p$ and $C_{m1}$ are recorded in the memories 5 and 6 respectively.

These determinations have been shown in solid line in FIG. 1.

The residue $E_R$ of the pyrolysis in an atmosphere of inert gas is placed into a heating chamber 7 which is preferably distinct from the heating chamber 1 for practical reasons.

The residue $E_R$ is then heated in an oxidizing atmosphere ($O_2$ and/or air) to a temperature $\theta_2$ which is at most equal to the temperature $\theta_1$. In order that the measurements be achieved over a sufficiently short time interval, $\theta_2$ is an isotherm temperature fixed at the value $\theta_1 - \Delta\theta$ with:

$0 < \Delta\theta < 50°$ C.

Thus only the organic carbon contained in the sample residue $E_R$ produces carbon dioxide $CO_2$ which is transmitted through a valve 30 and analyzed at 8 and from which the corresponding amount of organic carbon $C_R$ is determined. The so-obtained information is transmitted to the memory 5 where, the total amount of organic carbon "$C_{org\ total}$" contained is this sample is computed by adding the values $C_p$ and $C_R$.

Then, the temperature of the second heating chamber 7 is raised to a value $\theta_3$ capable of causing the decomposition of all the carbonated compounds contained in the sample and in particular those which decompose at a temperature higher than $\theta_1$.

The value $\theta_3$ of the temperature is thus selected higher than $\theta_1$ and, for example, equal to 1000° C. thus, providing for the decomposition of the carbonates, the main carbonates being calcite [$CaCO_3$], dolomite [$Ca\ Mg\ (CO_3)_2$] etc, whose thermal decomposition occurs above 600° C.

The carbon dioxide resulting from this decomposition of the carbonates is transmitted through the valve 30 to a device 9 which analyzes it and determines the corresponding amount $C_{m2}$ of mineral carbon.

This value is transmitted to the memory 6 where is added to the value $C_{m1}$ to give the total amount "$C_{min\ Total}$" of mineral carbon contained in the analyzed sample.

Optionally, if so required, the total amount of carbon may be obtained by adding the values.

$C_{org\ Total} + C_{min\ Total} = C_{Total}$

The advantages of the present invention are apparent from the above description.

As a matter of fact, by accurately knowing the total amount of organic carbon it is possible to evaluate the oil production characteristics of the sediments from which the sample has been collected. It will be obviously possible to distinguish the hydrocarbons originally present in the sample from the hydrocarbons produced by cracking of the organic material in an inert atmosphere, by first heating the sample in the first chamber 1 to a temperature $\theta'_1$ of about 300° C. providing for vaporization of the hydrocarbons present in the sample without cracking the organic material. It is even possible to distinguish between gaseous and liquid hydrocarbons by first heating the sample to a temperature $\theta''_1$ generally lower than 90° C. which permits degassing of the gaseous hydrocarbons contained in the sample, then to the temperature $\theta'_1$ providing for the vaporization of the liquid hydrocarbons originally present in the sample and finally to the temperature $\theta_1$ comprised between 500° and 600° C. which provides for cracking of the organic material.

The amount of mineral carbon is also a valuable information for determining the lithology of the ground levels traversed by a borehole.

Figure 2:
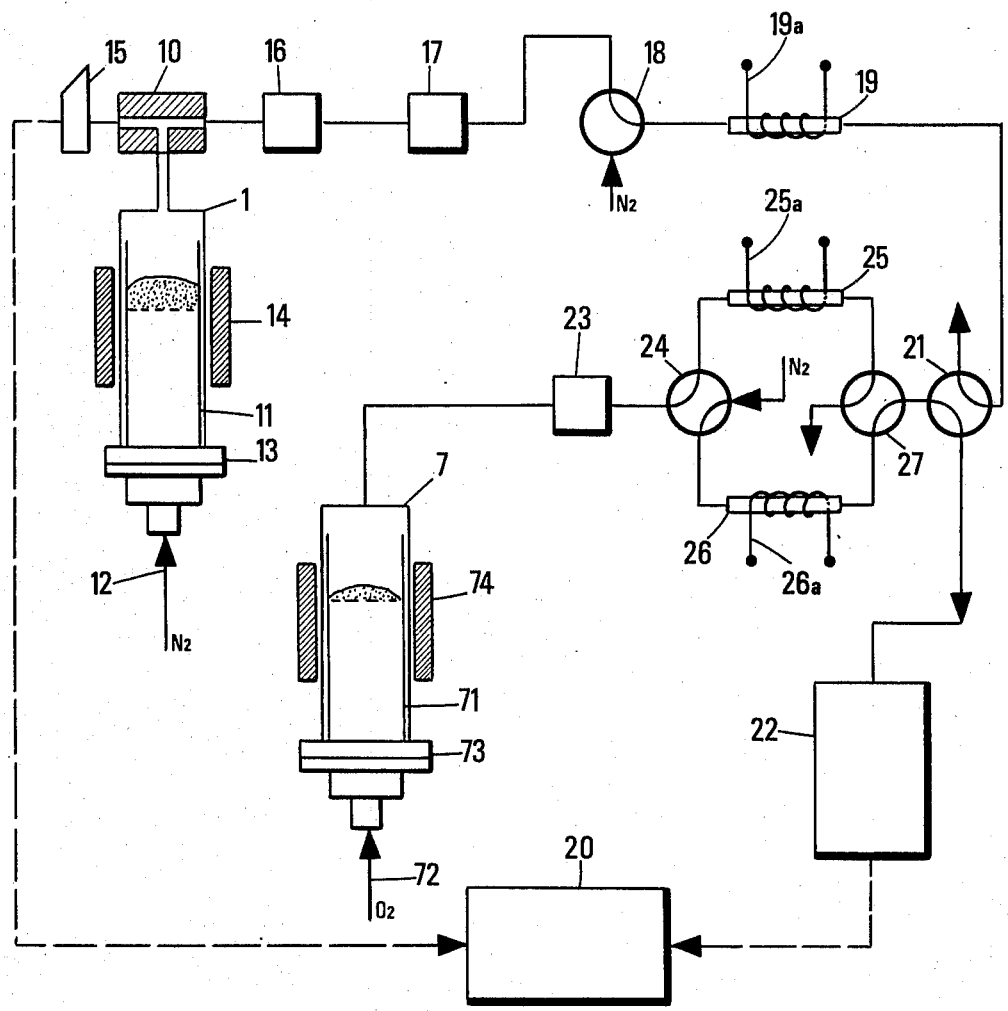
FIG. 2 diagrammatically shows an embodiment of the invention.

FIG. 2 diagrammatically shows an apparatus for carrying out the invention.

The apparatus comprises a first heating chamber 1, which in this embodiment is a sealed tubular housing preferably vertically positioned, into which a sample holder 11 can be introduced and which is fed with an inert gas such as nitrogen or helium through a pipe 12. Displacement of the holder 11 and sealing are ensured by a device diagrammatically shown at 13. This heating chamber is equipped with means 14 which may be of any known type such as electrical resistor, etc ensuring temperature rise within the heating chamber 1 to a temperature $\theta_1$ comprised between 500° and 600° C., but these means may also be adapted to maintain in the chamber 1 a constant temperature $\theta_1$.

Means for controlling and programming the heating means may be provided. They have not been shown so as to not complicate the drawings but their realization only requires only ordinary skill.

At its upper part, the heating chamber 1 communicates with a flow dividing device 10 which is preferably at the same temperature as the chamber 1 to prevent condensation phenomena from occurring in the effluent resulting from the cracking of the organic material.

This flow divider provides for the transfer of a determined fraction of the effluent to a suitable detector 15, such as, for example, a flame ionization detector which delivers a signal representing the organic carbon content of the effluent. This signal is transmitted to a suitably processing circuit 20 which comprises a suitable programmed microprocessor.

The remaining fraction of the effluent produced by the cracking of the organic material in an inert atmosphere first flows through a hydrocarbon trap 16, then through a water trap 17, which respectively retain the hydrocarbons condensing at room temperature and water contained in the pyrolysis products. By means of a three-way, two-position valve 18 the effluent flows through a device 19 where carbon dioxide is trapped before the effluent is discharged to the atmosphere through a four-way, two-position valve 21.

At the end of the pyrolysis step in an inert atmosphere which is conducted over a period of at least five minutes, the valves 18 and 21 are actuated so as to connect the carbon dioxide trap 19 with a source of inert gas such as helium, and with an apparatus 22 which is adapted to measure the amount of carbon dioxide received and to determine the corresponding carbon content.

Simultaneously, the trap 19 is heated by heating means 19 to cause desorption of $CO_2$.

The measuring apparatus 22 delivers a signal representing the mineral carbon content which is derived from the amount of carbon dioxide resulting from the decomposition of carbonated products contained in the sample up to the temperature $\theta_1$.

The residue of the pyrolysis in an inert atmosphere is then transferred into a second heating chamber 7 of the same type as the chamber 1.

This furnace is comprised of a vertically positioned tubular housing into which a sample holder 71 can be introduced, this housing being fed with air and/or oxygen $O_2$ through a pipe 72. Displacement of the sample holder 71 and sealing are achieved by means diagrammatically indicated at 73.

This heating chamber 7 is provided with means 74 which may be of any known-type, such as an electric resistor, providing for the temperature rise within the heating chamber 7.

These heating means are adapted to maintain in the chamber 7 during a first time interval a temperature $\theta_2$ at most equal to the value $\theta_1$, and preferably differing from $\theta_1$ by a value $\Delta\theta$ comprised between 0° and 50° C. By way of example, good results have been obtained by selecting the following temperatures $\theta_1 = 600°$ C. and $\theta_2 = 550°$ C. These heating means are also adapted to maintain in the furnace 7 during a second step following the first step, a temperature $\theta_3$ comprised between 750° C. and 1100° C. and more generally, close to 1000° C.

Means for controlling and programming the heating device 74 can be provided but are not shown in the drawings.

At its upper part the heating chamber 7 communicates with a device 23 for trapping water and can be alternatively connected with the devices 25 and 26 through a four-way, two-position valves 24, the first of these devices trapping the carbon dioxide resulting from the oxidation of the organic material at the temperature $\theta_2$, while the second device traps the carbon dioxide produced by the decompostion at the temperature $\theta_3$ of the carbonated products still present in the sample. The carbon dioxide adsorbed by the devices 25 and 26 can be desorbed by heating (between 250°–350° C.) by means of heating elements 25a and 26a, to be separately transmitted to the measuring apparatus 22 through a four-way, two-position valve 27, and the valve 21.

The so-effected measurements are transmitted to the processing circuit 20 which then delivers the required information, i.e. the total organic carbon and mineral carbon contents respectively.

To this end the processing circuit 20 may comprise a programmed micro-processor. This micro-processor may then be programmed to also automatically provide for the operation of the heating elements 14, 19a, 25a and 74, of the valves 18, 21, 24 and 27 and for the transfer of the sample from the chamber 1 to the chamber 7.

Figure 3:
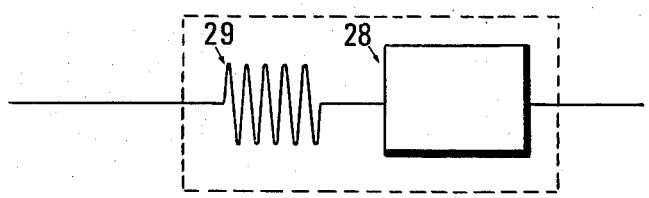
FIG. 3 schematically shows an embodiment of a device for determining the amount of carbon dioxide.

The carbon measuring apparatus 22 may be of any known type and may comprise a thermal conductivity detector or thermistor, or an infrared detector, etc, before which a chromatographic column 29 may optionally be located, as shown in FIG. 3.

Modifications may be made without departing from the scope of the invention.

For example, if only the total content of organic carbon is to be determined, only the corresponding steps of the method may be carried out.

What is claimed is:

1. A method for determining, the total organic carbon content of a sample of sediment, comprising the successive steps of:
   (a) heating a sample in an inert atmosphere to a first temperature capable of cracking at least a fraction of the organic material therein and to decompose all mineral carbonates decomposable up to said first temperature to produce a first effluent containing hydrocarbons, and a solid material residue,
   (b) measuring the amount of organic carbon contained in at least a fraction of the first effluent produced by said cracking of the organic material in an inert atmosphere, by selectively determining the amount of carbon in the hydrocarbons contained in said first effluent,
   (c) heating the solid material residue in an oxidizing atmosphere to a second temperature at most equal to said first temperature to produce a second effluent containing $CO_2$, said second temperature being insufficient to produce decomposition of remaining mineral carbonates contained in the residual material,
   (d) measuring the amount of organic carbon contained in the second effluent resulting from the oxidation of the organic material by measuring the amount of carbon in the $CO_2$ contained in said second effluent, and
   (e) deriving from the above measurements effected on said first and second effluents the total organic carbon content of the sample.

2. A method for determining the organic and mineral carbon content of a sample of sediment comprising the successive steps of:
   (a) heating a sample in an inert atmosphere to a first temperature capable of cracking at least a fraction of the organic material therein and to decompose all mineral carbonates decomposable up to said first temperature to produce a first effluent and a first residue,
   (b) measuring the amount of organic carbon contained in at least a fraction of the first effluent produced by said cracking of the organic material in an inert atmosphere, and measuring the quantity of mineral carbon contained in the remaining fraction of the first effluent,
   (c) heating the first residue of step (a) in an oxidizing atmosphere to a second temperature at most equal to said first temperature to produce a second effluent and a second residue,
   (d) measuring the amount of organic carbon contained in the second effluent resulting from the oxidation of the organic material in the first residue,
   (e) heating the second residue of step (c) in an oxidizing atmosphere to a third temperature capable of decomposing all the remaining mineral carbonates contained in the second residue to produce a third effluent,
   (f) measuring the quantity of mineral carbon contained in the third effluent, and
   (g) deriving from all the effected measurements the respective organic carbon and mineral carbon contents of the sample.

3. A method according to claim 2, wherein said heating steps comprise raising said first and second temperatures to 500°–600° C., and raising said third temperature to 750° C.–1100° C.

4. A method according to claim 3, wherein said third temperature is raised to near 1000° C.

5. A method according to claim 1, wherein said heating steps comprise raising said first and second temperatures to 500°–600° C.

6. A method according to claim 1 or 2, wherein said first heating step in an inert atmosphere is conducted for at least five minutes.

* * * * *